US012773237B2

(12) United States Patent
Horeman-Franse et al.

(10) Patent No.: US 12,773,237 B2
(45) Date of Patent: Oct. 27, 2026

(54) SURGICAL INSTRUMENT

(71) Applicant: PROVINCI SABEAIR B.V., The Hague (NL)

(72) Inventors: Tim Horeman-Franse, The Hague (NL); David Cefai, The Hague (NL)

(73) Assignee: PROVINCI SABEAIR B.V., The Hague (NL)

( * ) Notice: Subject to any disclaimer, the term of this patent is extended or adjusted under 35 U.S.C. 154(b) by 626 days.

(21) Appl. No.: 18/356,893

(22) Filed: Jul. 21, 2023

(65) Prior Publication Data

US 2023/0355273 A1 Nov. 9, 2023

Related U.S. Application Data

(63) Continuation of application No. PCT/NL2021/050768, filed on Dec. 16, 2021.

(30) Foreign Application Priority Data

Jan. 25, 2021 (NL) ..................................... 2027377

(51) Int. Cl.
*A61B 17/34* (2006.01)
*A61M 16/04* (2006.01)
(Continued)

(52) U.S. Cl.
CPC ...... *A61B 17/3474* (2013.01); *A61B 17/3415* (2013.01); *A61B 17/3496* (2013.01);
(Continued)

(58) Field of Classification Search
CPC ............ A61B 17/3496; A61B 17/3415; A61B 17/3474; A61B 2017/00424;
(Continued)

(56) References Cited

U.S. PATENT DOCUMENTS 5,364,365 A 11/1994 Wortrich
5,374,252 A 12/1994 Banks et al.
(Continued)

FOREIGN PATENT DOCUMENTS

BR PI0614821 A2 * 4/2011 ............. A61B 5/154
JP H11504234 A * 4/1999 ......... A61B 17/3496
(Continued)

OTHER PUBLICATIONS

BR-PI0614821, English language machine translation (Year: 2011).*
(Continued)

*Primary Examiner* — Wesley G Harris
(74) *Attorney, Agent, or Firm* — Peacock Law P.C.; Justin R. Muehlmeyer; Daniel J. Berenger-Russell

(57) ABSTRACT

A surgical instrument for piercing into a human or animal body. The instrument includes an inner portion which is movably arranged within an needle-like outer portion. The outer portion connects to the inner portion through a spring so as to provide with the outer portion during use a load on the inner portion. The outer portion includes a proximal sleeve that provides a finger grip to a person, likely a surgeon. The sleeve is releasably connectable to the outer portion and the instrument includes a release mechanism for releasing the sleeve from the outer portion, which release mechanism is actuable by motion of the inner portion.

5 Claims, 3 Drawing Sheets

(51) Int. Cl.
*A61B 17/00* (2006.01)
*A61M 16/08* (2006.01)

(52) U.S. Cl.
CPC .................... *A61M 16/0472* (2013.01); *A61B 2017/00424* (2013.01); *A61M 16/0465* (2013.01); *A61M 16/0816* (2013.01)

(58) Field of Classification Search
CPC ........ A61B 17/3417; A61B 2017/0046; A61B 2017/00477; A61M 16/0472; A61M 16/0465; A61M 16/0816
See application file for complete search history.

(56) References Cited

U.S. PATENT DOCUMENTS

| | | | | |
|---|---|---|---|---|
| 6,027,518 | A * | 2/2000 | Gaber | A61B 90/06 606/198 |
| 2007/0260184 | A1* | 11/2007 | Justis | A61B 17/16 604/164.01 |
| 2013/0310750 | A1* | 11/2013 | Hopman | A61B 17/3496 604/159 |
| 2015/0265777 | A1* | 9/2015 | Whitley | A61B 17/3496 604/512 |

FOREIGN PATENT DOCUMENTS

| | | | | |
|---|---|---|---|---|
| WO | WO-9404206 | A1 * | 3/1994 | A61B 17/3417 |
| WO | 2022158967 | A1 | 7/2022 | |

OTHER PUBLICATIONS

Dubois, Kayla , et al., "The Theia Soteria: Alternative Design for Safer Initial Entry During Laparoscopic Procedures", Union College, Honors Theses. 2289, 2019, 1-29.
Greenberg, James A., "LapCap", Rev Obstet Gynecol., vol. 1, No. 2, 2008, 84-85.
Nevler, Avinoam , et al., "Safer trocar insertion for closed laparoscopic access: ex vivo assessment of an improved Veress needle", Surg Endosc, vol. 30, 2016, 779-782.
Nillahoot, Nantida , et al., "Development of Veress Needle Insertion Robotic System and its experimental study for force acquisition in soft tissue", 2013 IEEE International Conference on Robotics and Biomimetics (ROBIO), 2013, 1.
Schaller, G., et al., "The optical "Veress-needle"—initial puncture with a minioptic", Endosc Surg Allied Technol., vol. 3, No. 1, 1995, 55-57.
Schaufler, Anna , et al., "Automatic differentiation between Veress needle events in laparoscopic access using proximally attached audio signal characterization", Current Directions in Biomedical Engineering, vol. 5, No. 1, 2019, 369-372.

* cited by examiner

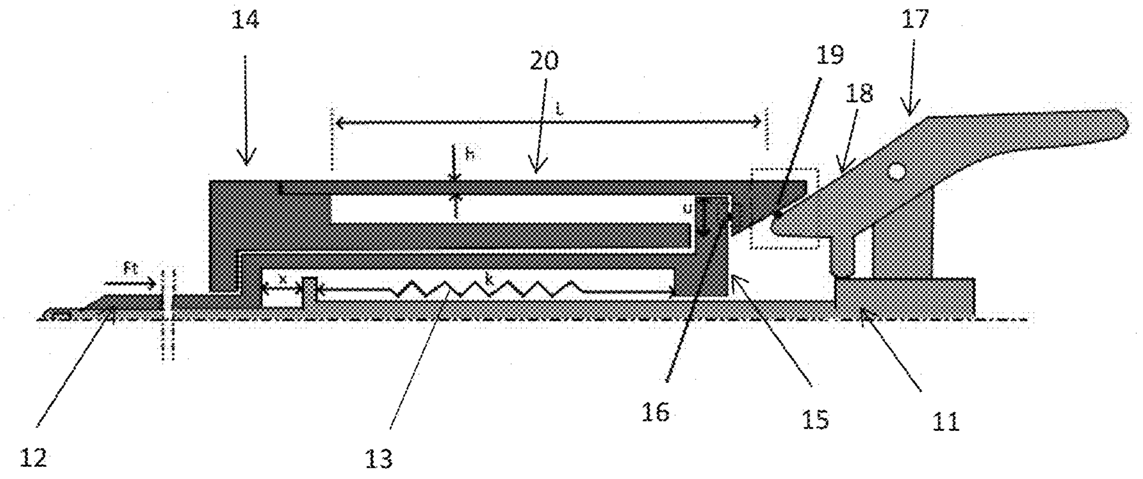
Fig.3 – Detail A
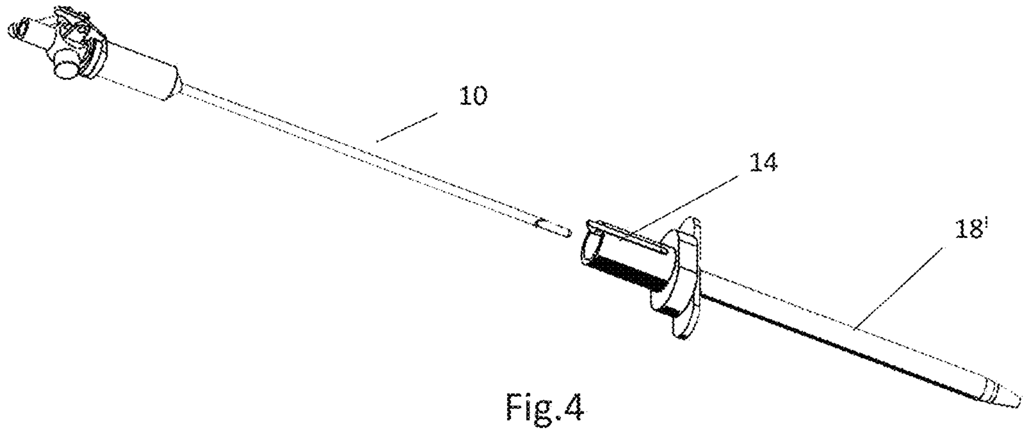
Fig.4

SURGICAL INSTRUMENT

CROSS-REFERENCE TO RELATED APPLICATIONS

This application is a continuation of International Patent Application No. PCT/NL2021/050768, titled "A Surgical Instrument", filed on Dec. 16, 2021, which claims priority to and the benefit of Netherlands Patent Application No. 2027377, titled "A Surgical Instrument", filed on Jan. 25, 2021, and the specification and claims thereof are incorporated herein by reference.

BACKGROUND OF THE INVENTION

Field of the Invention

The invention relates to a surgical instrument for piercing into a human or animal body, said instrument comprising an inner portion which is movably arranged within a needle-like outer portion, wherein said outer portion connects to the inner portion through a spring so as to provide with the outer portion during use a load on the inner portion, wherein said outer portion is provided with a proximal sleeve that provides a finger grip to a surgeon.

A typical example of a surgical instrument used for similar purposes is a Veress needle, hereinafter referred to as VN. The known VN is used to gain initial access to a peritoneal cavity of a patient to establish pneumoperitoneum. The use of the VN involves a blind insertion into the peritoneal cavity of the patient.

The use of the VN is probably popular because of its simplicity and effectiveness. It involves making a small incision in or near the umbilicus or in the left upper quadrant of the abdomen and then, in a blind fashion, putting the needle through the subcutaneous tissue, abdominal wall and the parietal peritoneum into the abdominal cavity. The VN technique is based on the ability of its blunt inner stylet to spring forward (since it is spring loaded) and to cover the sharp bevelled tip outer cannula when resistance diminishes after all tissue layers are passed. However, the surgeon cannot totally rely on this mechanism and therefore needs to develop a sense of the appropriate angle of insertion and the appropriate force to successfully puncture through the abdominal wall without overshooting into the underlying organs. The risk of damaging the underlying tissue with the tip of the cannula becomes high, when the reaction force that is generated by the abdominal wall drops to nearly zero (inside the abdominal cavity) in an instant. This immediate loss of resistance on the tip of the VN after puncturing causes acceleration of the needle towards the underlying tissues due to the slow reaction of the human control system, absence of stiff lower arm/hand support and relatively large mass of the surgeon's arm. Therefore, skilled and safe use of the VN requires a long learning curve to achieve the best possible instrument handling to prevent overshoot. Moreover, every patient's abdomen presents unique operating conditions, of which the specifics are unknown to the surgeon prior to the operation. These include the presence of adhesions, positions of the underlying tissues and viscera and the thickness of the abdominal wall.

Background Art

There are some existing instruments that attempt to counter the above-mentioned problem of overshooting.

US2015/0265777 proposes an instrument wherein the surgeon sets a maximal insertion depth. Unfortunately, the tissue layer thickness is not always known, and layers are flexible making adjustment of the insertion depth difficult.

U.S. Pat. No. 5,364,365 allows overshooting but fixates the Veress mechanism as soon as it shoots in position. It seems however possible that even a blunt stylet with locked outer cannula can easily damage internal structures.

The articles by Nevler, A., Har-Zahav, G., Rosin, D., & Gutman, M. (2016); Safer trocar insertion for closed laparoscopic access: ex vivo assessment of an improved Veress needle. Surgical endoscopy, 30(2), 779-782, and by DuBois, K., Ryan, P., & Joanis, M. (2019). The Theia Soteria: Alternative Design for Safer Initial Entry During Laparoscopic Procedures focus on expanding the blunt area of the tip directly after insertion in order to reduce the stress when the tip hits underlying organs or structures.

The articles by Schaufler, A., San, T., Esmaeili, N., Boese, A., Wex, C., Croner, R., . . . & Illanes, A. (2019). Forcematic differentiation between Veress needle events in laparoscopic access using proximally attached audio signal characterization. Current Directions in Biomedical Engineering, 5(1), 369-371, and by Schaller, G., Kuenkel, M., & Manegold, B. C. (1995). The optical "Veress-needle"—initial puncture with a minioptic. Endoscopic surgery and allied technologies, 3(1), 55-57, report on the possibility to acquire information about intracorporeal tissue tool interactions of the VN tip, utilizing acoustic emissions or optic information recorded at the extracorporeal end of the needle.

The article by Greenberg, J. A. (2008). LapCap™. Reviews in Obstetrics and Gynecology, 1(2), 84 teaches to create a vacuum cup around the VN. When sucking the air out of the cup the abdominal wall is lifted away from the critical structures when the VN penetrates the tissue. A disadvantage here is that the surgeon loses manipulation flexibility as the configuration of the needle is fixed.

Finally, overshooting can be prevented by introducing a faster control system. This can be done by linking a robot arm with haptic sensation to the VN's body that generates the driving force, as is suggested by Nillahoot, N., & Suthakorn, J. (2013, December). Development of Veress needle insertion robotic system and its experimental study for force acquisition in soft tissue. In 2013 IEEE International Conference on Robotics and Biomimetics (ROBIO) (pp. 645-650). IEEE.

Although some of the proposals show interesting results, the complex nature of the proposed systems and the impact on workflow jeopardizes broader acceptance. It is therefore an object of the invention to provide a surgical instrument which is devoid of the complications of the known proposals, and which impairs the surgeon's operations as little as possible, so as to keep close to the surgeon's existing operational practices.

This application refers to other publications to provide a more complete background. Such references are not to be construed as an admission that such references are prior art for purposes of determining the patentability of the present invention.

BRIEF SUMMARY OF THE INVENTION

Embodiments of the present invention are directed to a surgical instrument as claimed in this application. It is noted that although the previous discussion concentrates on the application of a VN, as the above recited preamble indicates the invention has broader application and relates to any surgical instrument for piercing into a human or animal body, wherein said instrument comprises an inner portion which is movably arranged within an needle-like outer portion, wherein said outer portion connects to the inner portion through a spring so as to provide with the outer portion during use a load on the inner portion, and wherein said outer portion is provided with a proximal sleeve that provides a finger grip to a surgeon. Examples thereof are for instance direct sharp trocar entries during laparoscopic surgery, and chest tube thoracostomies emergency or elective surgical airway.

US2013/0310750 discloses an instrument comprising a sleeve that is releasably connectable to the outer portion and the instrument is provided with a release mechanism for releasing the sleeve from the outer portion, which release mechanism is actuable by motion of the inner portion.

In the instrument of the invention, the outer portion is provided with a proximal ring or edge, and the sleeve is provided with a displaceable hook for hooking behind the ring or edge and thus provide a connection between the outer portion and the sleeve, wherein the release mechanism can be operable on the hook to remove it from its position behind the ring or edge. This makes possible that when the sleeve is used by the surgeon or a robot to push and insert the outer portion in the peritoneal cavity of a patient, the sudden drop of resistance when the insertion is accomplished and which is followed by an immediate forward movement of the spring-loaded inner portion, will have the effect that the inner portion activates the release mechanism which then neutralizes the driving force that the surgeon or robot applies to the sleeve, due to its release from the outer portion.

Suitably the release mechanism is mounted proximal on the inner portion and is arranged to operate on the hook of the sleeve when the inner portion moves towards the sleeve so as to release the sleeve from the outer portion.

The construction of the surgical instrument of the invention can be operationally effective and still be provided at limited cost when the release mechanism comprises a slanting first contact surface that is tailored to a correspondingly slanting second contact surface that is provided on the hook.

It is preferred that the hook is resiliently mounted on the sleeve so as to provide that the hook is displaced from its position behind the ring or edge of the outer portion at the time that the slanting first contact surface of the release mechanism impacts the second contact surface that is provided on the hook.

Suitably the release mechanism comprises a lever arm which is mounted proximal on the inner portion.

Optionally the proximal sleeve of the instrument is provided with an extension comprising one of a breathing tube or trocar tube. This relates to using the surgical instrument of the invention for intubating the trachea or intubating the abdominal wall with a trocar, respectively.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 3 is an illustration showing a detailed side cross-sectional view of the proximal portion of the Veress needle shown in FIG. 2 according to an embodiment of the present invention; and FIGS. 4 and 5 are illustrations showing a perspective view of a surgical instrument in an application for intubating the trachea or intubating the abdominal wall with a trocar, respectively, according to an embodiment of the present invention.

DETAILED DESCRIPTION OF THE INVENTION

Figure 1:
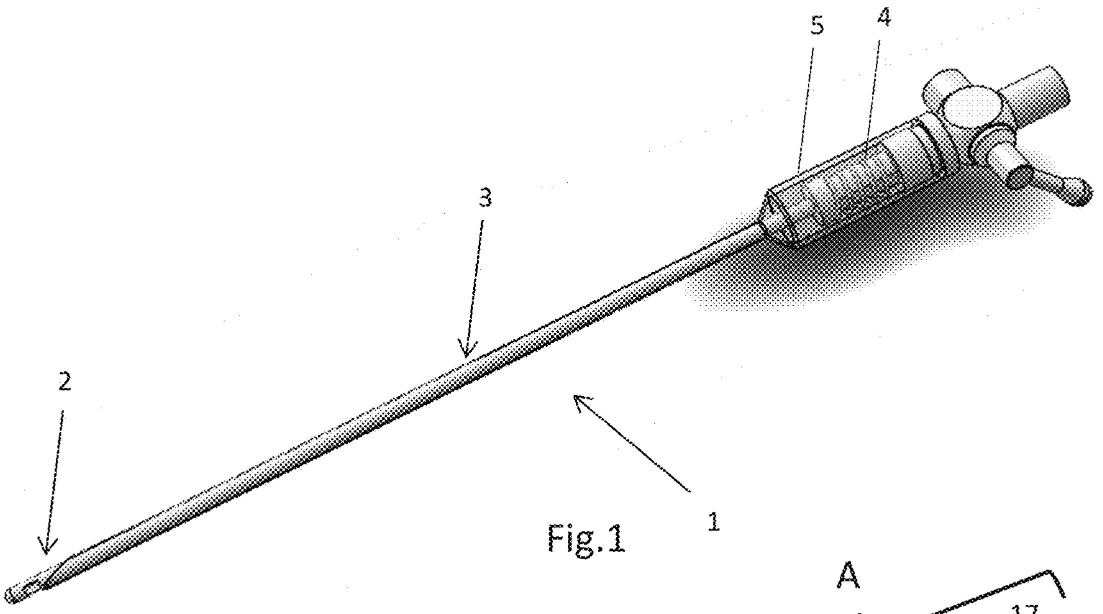
FIG. 1 is an illustration showing a perspective view and partial cross-sectional view of a Veress needle according to the prior art.

Whenever in the figures the same reference numerals are applied, these numerals refer to the same or similar parts.

Figure 2:
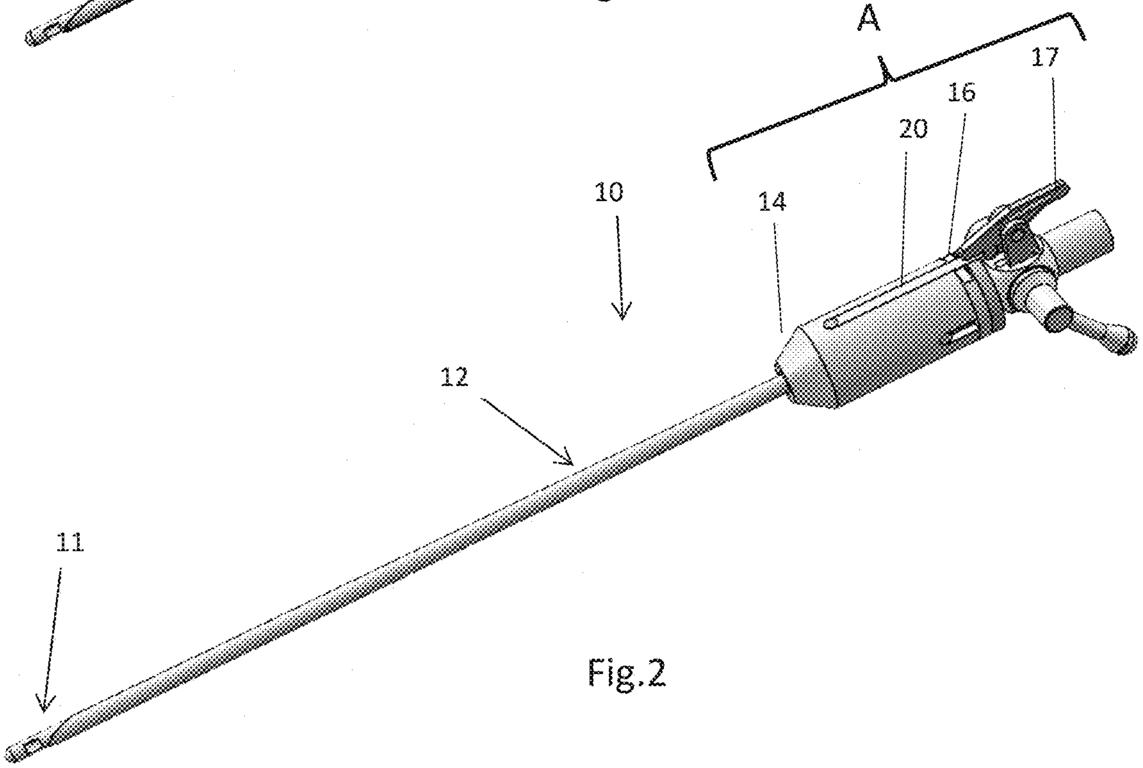
FIG. 2 is an illustration showing a perspective view of a Veress needle according to an embodiment of the present invention.

A Veress needle as shown in the figures is used for piercing into a human or animal body. As shown in FIG. 1 and in FIG. 2, instrument 1, 10 comprises inner portion 2, 11 which is movably arranged within needle-like outer portion 3, 12, wherein outer portion 3, 12 connects to inner portion 2, 11 through a spring. In the prior art instrument 1, the spring is depicted with reference 4. The detail A of the proximal portion of the instrument 10 of the invention which is shown in FIG. 3, shows the spring as being depicted with reference 13.

Both in the prior art instrument 1 and in instrument 10 of the invention, the spring serves to apply with outer portion 3, 12 during use a load on inner portion 2, 11. In connection therewith outer portion 3, 12 is provided with proximal sleeve 5, 14 that provides a finger grip for a surgeon. So far, prior art instrument 1 and instrument 10 of the invention have corresponding features, albeit that the construction of proximal sleeve 5 of instrument 1 differs from proximal sleeve 14 of instrument 10.

Instrument 10 of the invention differentiates from the prior art in that sleeve 14 is releasably connectable to outer portion 12 and that instrument 10 is provided with a release mechanism for releasing sleeve 14 from outer portion 12, which release mechanism is actuable by motion of inner portion 11. The manner in which this can be preferably embodied is further explained with reference to the detail of the instrument of the invention as depicted in FIG. 3.

In FIG. 3 it is shown that outer portion 12 is provided with proximal ring or edge 15, and that sleeve 14 is provided with displaceable hook 16 for hooking behind ring or edge 15 and thus provide a connection between outer portion 12 and sleeve 14. Release mechanism 17, which comprises a lever arm mounted proximal on inner portion 11 can then be operable on hook 16 to remove it from its position behind ring or edge 15 according to the following elucidation.

Release mechanism 17 is mounted proximal on inner portion 11 and is arranged to operate on hook 16 of sleeve 14 when inner portion 11 moves towards sleeve 14 so as to release sleeve 14 from outer portion 12. To that end it is preferable that release mechanism 17 comprises a slanting first contact surface 18 that is tailored to a correspondingly slanting second contact surface 19 that is provided on hook 16. Hook 16 is resiliently mounted on sleeve 14 by means of the resilient support 20 so as to provide that hook 16 can be displaced from its position behind ring or edge 15 of outer portion 12 at the time that slanting first contact surface 18 of release mechanism 17 impacts second contact surface 19 that is provided on hook 16.

Turning now to FIG. 4, the surgical instrument of the invention is shown wherein proximal sleeve 14 is provided with an extension in the form of breathing tube 18'. This construction is used for intubating the trachea. After piercing, all parts of instrument 10 except for sleeve 14 with breathing tube 18' shoot backwards and can be removed from the surgical site. Then proximal sleeve 14 is removed from breathing tube 18 that remains in place for breathing.

Figure 5:
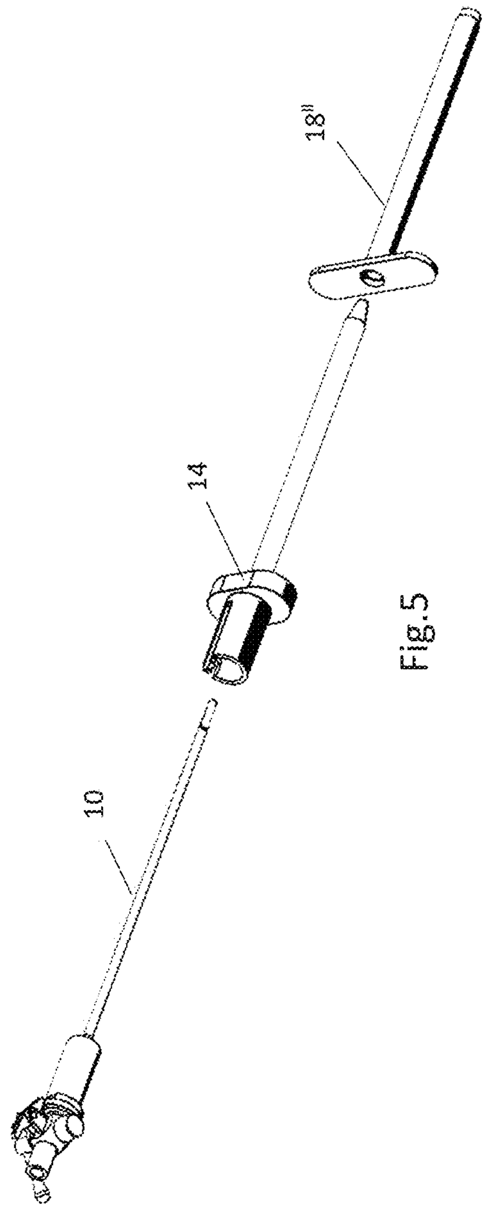

FIG. 5 shows another application which is used for piercing the abdominal wall with a trocar. After piercing, all parts of instrument 10 except for sleeve 14 with an extension embodied as trocar tube 18' shoot backwards and can be removed from the surgical site. Then proximal sleeve 14 is removed from trocar tube 18" that remains in place for instrument guidance towards the abdominal cavity.

Although the invention has been discussed in the foregoing with reference to an exemplary embodiment of the surgical instrument of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another. The terms, "a", "an", "the", and "said" mean "one or more" unless context explicitly dictates otherwise.

The invention claimed is:

1. A surgical instrument for piercing into a human or animal body, the instrument comprising:

an inner portion which is movably arranged within a needle-like outer portion, wherein the outer portion connects to the inner portion through a spring so as to provide with the outer portion during use a load on the inner portion, wherein the outer portion is provided with a proximal sleeve that provides a finger grip to a person, wherein the sleeve is releasably connectable to the outer portion; and a release mechanism for releasing the sleeve from the outer portion, which the release mechanism is actuable by motion of the inner portion, wherein the outer portion is provided with a proximal ring or edge; and the sleeve comprises a displaceable hook for hooking behind the ring or edge to provide a connection between the outer portion and the sleeve, wherein the release mechanism can be operable on the hook to remove it from its position behind the ring or edge, and wherein the release mechanism is mounted proximal on the inner portion and is arranged to operate on the hook of the sleeve when the inner portion moves towards the sleeve so as to release the sleeve from the outer portion.

2. The surgical instrument of claim 1, wherein the release mechanism comprises a slanting first contact surface that is tailored to a correspondingly slanting second contact surface disposed on the hook.

3. The surgical instrument of claim 2, wherein the hook is resiliently mounted on the sleeve so as to provide that the hook is displaced from its position behind the ring or edge of the outer portion at the time that the slanting first contact surface of the release mechanism impacts the second contact surface that is provided on the hook.

4. The surgical instrument of claim 1, wherein the release mechanism comprises a lever arm which is mounted proximal on the inner portion.

5. The surgical instrument of claim 1, wherein the proximal sleeve comprises an extension comprising one of a breathing tube or trocar tube.

* * * * *